(12) United States Patent
McConville et al.

(10) Patent No.: US 6,518,444 B1
(45) Date of Patent: Feb. 11, 2003

(54) PREPARATION OF POLYMERIZATION CATALYSTS

(75) Inventors: David H. McConville, Houston, TX (US); Jaimes Sher, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 209 days.

(21) Appl. No.: 09/739,176

(22) Filed: Dec. 18, 2000

(51) Int. Cl.[7] .............. C07F 7/00; B01J 31/00; C08F 4/44

(52) U.S. Cl. .............. 556/52; 556/18; 556/21; 556/42; 556/51; 556/57; 502/103; 502/120; 526/139; 526/140; 526/141; 526/142

(58) Field of Search .............. 556/42, 51, 52, 556/57, 18, 21; 502/103, 120; 526/139, 140, 141, 142

(56) References Cited

U.S. PATENT DOCUMENTS 3,914,311 A   10/1975   Coulson .............. 260/577
5,233,090 A   8/1993    Shimada et al. .............. 564/426
5,319,069 A   6/1994    Sasaki et al. .............. 528/425
5,382,692 A   1/1995    Shimada et al. .............. 564/426
5,403,950 A   4/1995    Shimada et al. .............. 558/418
5,576,460 A   11/1996   Buchwald et al. .............. 564/386
5,889,128 A   3/1999    Schrock et al. .............. 526/107
5,929,281 A   7/1999    Nishiyama et al. .............. 564/386

FOREIGN PATENT DOCUMENTS

EP   0 802 173 A   10/1997
WO   WO 0002887 A   1/2000

OTHER PUBLICATIONS

*Tetrahedron Letters*, vol. 25, No. 30, 1984, pp. 3175–3178.
Shukla, P.R. et al., "*Copper(II) and Nickel(II) Complexes with N1, N3–bis(2,4–dinitrophenyl)diethylenetriamine, N1, n4–bis(2,4–diaminophenyl) derivatives*", J. Indian Chem. Soc., 1987, vol. 64, No. 12, 722–724.

*Primary Examiner*—Porfirio Nazario-Gonzalez

(57) ABSTRACT

A method to synthesize a Group 15 containing metal polymerization catalyst is disclosed. The method includes an efficient high temperature synthesis of Group 15 containing ligands, especially arylamine ligands, for use in preparing polymerization catalysts and catalyst systems.

16 Claims, No Drawings

PREPARATION OF POLYMERIZATION CATALYSTS

FIELD OF THE INVENTION

This invention relates to a method to synthesize Group 15 containing metal polymerization catalyst compounds. More specifically, this invention relates to a method to synthesize Group 15 containing ligands, and especially arylamine ligands, for use in the preparation of Group 15 containing metal polymerization catalyst compounds.

BACKGROUND OF THE INVENTION

The commercialization of metallocene polyolefin catalysts (metallocene being cyclopentadienyl based transition metal catalyst compounds) has led to widespread interest in the design and preparation of other catalysts and catalyst systems, particularly for use in economical gas and slurry phase processes.

Anionic, multidentate heteroatom ligands have received attention in polyolefins catalysis. Notable classes of bidentate anionic ligands which form active polymerization catalysts include N—N⁻ and N—O⁻ ligand sets. Examples of these types catalysts include amidopyridines. (Kempe, R., "Aminopyridinato Ligands—New Directions and Limitations", 80$^{th}$ Canadian Society for Chemistry Meeting, Windsor, Ontario, Canada, Jun. 1–4, 1997; Kempe, R. et al., *Inorg. Chem.* 1996 vol. 35 6742.) Likewise, recent reports by Jordan et al. disclose polyolefin catalysts based on hydroxyquinolines. (Bei, X.; Swenson, D. C.; Jordan, R. F., *Organometallics* 1997, 16, 3282).

U.S. Pat. No. 5,576,460 to Buchwald et al. discloses two synthesis routes to preparing arylamine compounds. The first route includes reacting a metal amide comprising a metal selected from the group consisting of tin, boron, zinc, magnesium, indium and silicon, with an aromatic compound comprising an activated substituent in the presence of a transition metal catalyst to form an arylamine. The second route utilizes an amine rather than a metal amide. The '460 patent teaches that this reaction be conducted at a temperature of less than about 120° C. and is drawn to the use of the arylamine as an intermediate in pharmaceutical and agricultural applications.

U.S. Pat. No. 5,929,281 to Nishiyama et al. discloses the preparation of a heterocyclic aromatic amines in the presence of a catalyst system comprising a palladium compound and a tertiary phosphine and the preparation of arylamines in the presence of a catalyst system comprising a palladium compound and a trialkylphosphine.

U.S. Pat. No. 3,914,311 to Coulson discloses a low temperature method of preparing an arylamine by the reaction of an amine with an aromatic compound having a displaceable activated substituent at temperatures as low as 25° C. in the presence of nickel catalyst and a base.

Boger et al in "Palladium (O) Mediated β-Carboline Synthesis: Preparation of the CDE Ring System of Lavendamycin" 25 Tetrahedron Letters, No. 30, pp. 3175–78 (1984) discloses low temperature preparation of arylamines by reacting an amine with an aromatic compound containing an activated substituent at 80° C. or 100° C. in the presence of a palladium catalyst and a base.

There is a need in the art for new methods to synthesize anionic, multidentate heteroatom ligands for use in polymerization catalyst systems.

SUMMARY OF THE INVENTION

The present invention relates to a method to synthesize a Group 15 containing metal polymerization catalyst. In another respect the invention relates to an efficient high temperature synthesis of Group 15 containing ligands, especially arylamine ligands, for use in preparing polymerization catalysts and catalyst systems.

Specifically, the arylamine is prepared by reacting an amine and an aromatic compound having suitable leaving groups at a temperature above 120° C. and preferably above 130° C.

DETAILED DESCRIPTION OF THE INVENTION

Introduction

The present invention provides a method to synthesis a Group 15 containing metal polymerization catalyst compound defined below. Generally, the method includes a new efficient high temperature preparation of the Group 15 atom containing ligand.

Group 15 Containing Metal Polymerization Catalyst Compound

The Group 15 containing metal polymerization catalyst compounds, which may be prepared by the method of the present invention, generally include a Group 3 to 14 metal atom, preferably a Group 3 to 7, more preferably a Group 4 to 6, and even more preferably a Group 4 metal atom, bound to at least one leaving group and also bound to at least two Group 15 atoms, at least one of which is also bound to a Group 15 or 16 atom through another group. The Group 15 atoms of the catalyst compound are also bound to a Group 15 or 16 atom through another group which may be a $C_1$ to $C_{20}$ hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and may optionally be bound to hydrogen, a halogen, a heteroatom or a hydrocarbyl group, or a heteroatom containing group.

In another embodiment, the Group 15 containing metal catalyst compound, prepared by the method of the present invention is represented by the formulae:

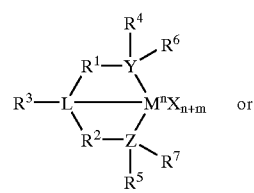

Formula (I)

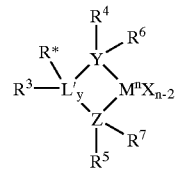

Formula (II)

wherein:

M is a Group 3 to 12 transition metal or a Group 13 or 14 main group metal, preferably a Group 4, 5, or 6 metal, and more preferably a Group 4 metal, and most preferably zirconium, titanium or hafnium;

each X is independently a leaving group, preferably, an anionic leaving group, and more preferably hydrogen, a hydrocarbyl group, a heteroatom or a halogen, and most preferably an alkyl;

y is 0 or 1 (when y is 0 group L' is absent);

n is the oxidation state of M, preferably +3, +4, or +5, and more preferably +4;

m is the formal charge of the YLZ or the YL'Z ligand, preferably 0, −1, −2 or −3, and more preferably −2;

L is a Group 15 or 16 element, preferably nitrogen;

L' is a Group 15 or 16 element or Group 14 containing group, preferably carbon, silicon or germanium;

Y is a Group 15 element, preferably nitrogen or phosphorus, and more preferably nitrogen;

Z is a Group 15 element, preferably nitrogen or phosphorus, and more preferably nitrogen;

$R^1$ and $R^2$ are independently a $C_1$ to $C_{20}$ hydrocarbon group, a heteroatom containing group having up to twenty carbon atoms, silicon, germanium, tin, lead, or phosphorus, preferably a $C_2$ to $C_{20}$ alkyl, aryl or aralkyl group, more preferably a linear, branched or cyclic $C_2$ to $C_{20}$ alkyl group, most preferably a $C_2$ to $C_6$ hydrocarbon group;

$R^3$ is absent or a hydrocarbon group, hydrogen, a halogen, a heteroatom containing group, preferably a linear, cyclic or branched alkyl group having 1 to 20 carbon atoms, more preferably $R^3$ is absent, hydrogen or an alkyl group, and most preferably hydrogen;

$R^4$ and $R^5$ are independently an alkyl group, an aryl group, substituted aryl group, a cyclic alkyl group, a substituted cyclic alkyl group, a cyclic aralkyl group, a substituted cyclic aralkyl group or multiple ring system, preferably having up to 20 carbon atoms, more preferably between 3 and 10 carbon atoms, and even more preferably a $C^1$ to $C_{20}$ hydrocarbon group, a $C_1$ to $C_{20}$ aryl group or a $C_1$ to $C_{20}$ aralkyl group, or a heteroatom containing group, for example $PR_3$, where R is an alkyl group, $R^1$ and $R^2$ may be interconnected to each other, and/or $R^4$ and $R^5$ may be interconnected to each other;

$R^6$ and $R^7$ are independently absent, or hydrogen, an alkyl group, halogen, heteroatom or a hydrocarbyl group, preferably a linear, cyclic or branched alkyl group having 1 to 20 carbon atoms, more preferably absent; and R* is absent, or is hydrogen, a Group 14 atom containing group, a halogen, a heteroatom containing group.

By "formal charge of the YLZ or YL'Z ligand", it is meant the charge of the entire ligand absent the metal and the leaving groups X.

By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups.

An alkyl group may be a linear, branched alkyl radicals, or alkenyl radicals, alkynyl radicals, cycloalkyl radicals or aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In a preferred embodiment $R^4$ and $R^5$ are independently a group represented by the following Formula (III):

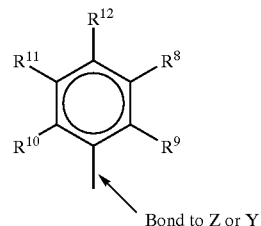

Formula (III)

wherein $R^8$ to $R^{12}$ are each independently hydrogen, a $C_1$ to $C_{40}$ alkyl group, a halide, a heteroatom, a heteroatom containing group containing up to 40 carbon atoms, preferably a $C_1$ to $C_{20}$ linear or branched alkyl group, preferably a methyl, ethyl, propyl or butyl group, any two R groups may form a cyclic group and/or a heterocyclic group. The cyclic groups may be aromatic. In a preferred embodiment $R^9$, $R^{10}$ and $R^{12}$ are independently a methyl, ethyl, propyl or butyl group (including all isomers), in a preferred embodiment $R^9$, $R^{10}$ and $R^{12}$ are methyl groups, and $R^8$ and $R^{11}$ are hydrogen.

In a particularly preferred embodiment $R^4$ and $R^5$ are both a group represented by the following Formula (IV):

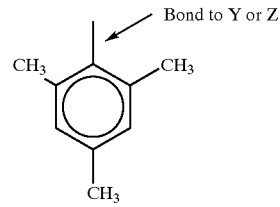

Formula (IV)

In this embodiment, M is a Group 4 metal, preferably zirconium, titanium or hafnium, and even more preferably zirconium; each of L, Y, and Z is nitrogen; each of $R^1$ and $R^2$ is —$CH_2$—$CH_2$—; $R^3$ is hydrogen; and $R^6$ and $R^7$ are absent.

In a particularly preferred embodiment the Group 15 containing metal catalyst compound, is represented by Compound (I), below, where Ph denotes a phenyl group:

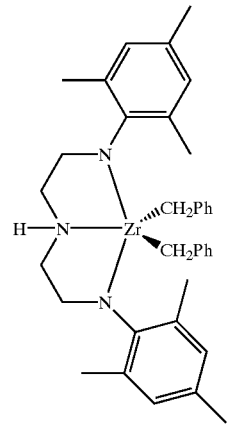

Compound (I)

Preparation of the YLZ or YL'Z Ligand

The method of the invention is directed to the preparation of the YLZ and the YL'Z ligands of Formulae (I) and (II)

above. The YLZ ligand of Formula (I) above may be prepared according to Reaction (I), and the YL'Z ligand of Formula (II) maybe prepared according to Reaction (II).

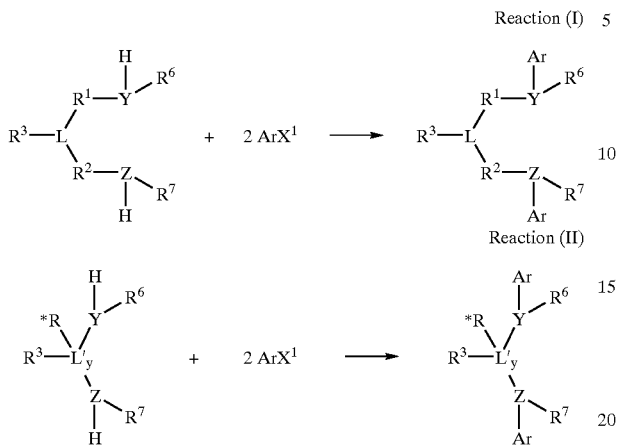

Reaction (I)

Reaction (II)

In Reactions (I) and (II) ArX$^1$ is an aromatic compound having at least one leaving group X$^1$. Aromatic compound ArX$^1$ includes those derived from simple aromatic rings, or heteroaromatic rings, such as for example, pyridine, quinoline, furan, pyrrole, and thiophene, and fused ring systems, such as for example, naphthalene, anthracene, tetralin, imidizole, and indole. The aromatic compound may be unsubstituted or have one or more substituents bound to the aromatic ring. Non-limiting examples of substituents include alkyl, aryl, acyl, heteroaryl, amino, carboxylic ester, carboxylic acid, a hydrogen group, ether, thioether, amide, carboxamide, nitro, phosphonic acid, suphonic acid, halide, pseudohalide groups and substituted derivatives thereof. In a preferred embodiment, each Ar of the compound ArX$^1$ utilized in the method of the invention, is independently represented as described for R$^4$ and R$^5$ above. In a most preferred embodiment, each Ar of the compound ArX$^1$ utilized in the method of the invention, is independently represented by Formula (III) or (IV) described above.

Each X$^1$ is independently a suitable leaving group and preferably, an anionic leaving group. Preferably, each X$^1$ is independently a hydrogen, a hydrocarbyl group, a heteroatom, a halogen, or an alkyl, preferably a halogen. Non-limiting examples of suitable leaving group X$^1$ include chloride, bromide, iodide, triflate, mesylate tosylate diazonium, and SR where R is aryl or alkyl. More preferably each X$^1$ is a halogen. In a most preferred embodiment, X$^1$ of the ArX$^1$ compound utilized in the method of the present invention, is bromide.

In Reactions (I) and (II), L is a Group 15 or 16 element, preferably a Group 15 element and most preferably nitrogen;

L' is a Group 15 or 16 element or Group 14 containing group, preferably carbon, silicon or germanium, y is 0 or 1 (when y is 0 groups L', R* and R$^3$ are absent);

Y is a Group 15 element, preferably nitrogen or phosphorus, and more preferably nitrogen;

Z is a Group 15 element, preferably nitrogen or phosphorus, and more preferably nitrogen;

R$^1$ and R$^2$ are independently a C$_1$ to C$_{20}$ hydrocarbon group, a heteroatom containing group having up to twenty carbon atoms, silicon, germanium, tin, lead, or phosphorus, preferably a C$_2$ to C$_{20}$ alkyl, aryl or aralkyl group, more preferably a linear, branched or cyclic C$_2$ to C$_{20}$ alkyl group, most preferably a C$_2$ to C$_6$ hydrocarbon group.

R$^3$ is hydrogen, a hydrocarbon group, a halogen, a heteroatom containing group, preferably a linear, cyclic or branched alkyl group having 1 to 20 carbon atoms, more preferably R$^3$ is hydrogen or an alkyl group, and most preferably R$^3$ is hydrogen R$^1$ and R$^2$ may be interconnected to each other as described above;

R$^6$ and R$^7$ are independently hydrogen, an alkyl group, halogen, heteroatom or a hydrocarbyl group, preferably hydrogen, a linear, cyclic or branched alkyl group having 1 to 20 carbon atoms, most preferably R$^6$ and R$^7$ are hydrogen;

R* is absent, or is hydrogen, a Group 14 atom containing group, a halogen, a heteroatom containing group.

Preferably, Reactions (I) and (II) are conducted in the presence of a suitable transition metal catalyst and a base. Non-limiting examples of suitable transition metal catalysts include complexes of platinum, palladium, iron, nickel, ruthenium and rhodium. Catalyst complexes may include chelating ligands, such as by way of example only, alkyl and aryl derivatives of phosphines and bisphosphines, imines, arsines, and hybrids thereof, including hybrids of phosphines with amines. Additionally, heterogeneous catalysts containing forms of these elements are also suitable catalysts for any of the transition metal catalyzed reactions of the present invention. Catalysts containing palladium and nickel are preferred. In a most preferred embodiment, the catalyst utilized in the method of the present invention includes tris(dibenzylideneacetone)dipalladium and rac-2,2'-bis(diphenylphosphino)-1,1'-binaphthyl (racemic BINAP).

Any suitable organic or inorganic base or combination of bases may be utilized in the method of the present invention. Non-limiting examples of suitable bases include Na$_2$CO$_3$ K$_2$CO$_3$, Tl$_2$CO$_3$, CsCO$_3$, K(t-BuO), Na(t-BuO), K(OPh), Na(OPh) or mixtures thereof where t-Bu represents tert-butyl and where Ph represents phenyl. In a most preferred embodiment the base utilized in the method of the present invention is Na(t-BuO).

In Reactions (I) and/or (II), in one embodiment, L, Y and Z are independently a Group 15 atom. In another embodiment L, Y, and Z are nitrogen. In another embodiment, R$^3$, R$^6$ and R$^7$ are hydrogen and the transition metal catalyst includes tris(dibenzylideneacetone)dipalladium and rac-2,2'-bis(diphenylphosphino)-1,1'-binaphthyl (racemic BINAP).

Reactions (I) and (II) may be carried out at any suitable pressure under an inert atmosphere. Preferably, the reactions are carried out at atmospheric pressure under nitrogen.

Reactions (I) and (II) may be carried out an any suitable temperature, but are most efficient when carried out at a temperature above 120° C., preferably above 125° C., more preferably above 130° C. and even more preferably above 140° C. In another embodiment, Reactions (I) and (II) are carried out a temperature between about 120 to about 200° C., more preferably between about 125 and 180° C. It has been determined that higher reaction temperatures especially benefit the formation of bulkier arylamine compounds such as those derived when Ar of ArX in Reactions (I) and (II) include relatively large substituents and or comprise a fused ring system. In addition, the higher reaction temperatures produces higher product yield at a faster rate of reaction.

Reactions (I) and (II) are typically carried out in any suitable solvent. Preferably, the solvent does not adversely affect the reaction and has a boiling point above the reaction temperature. In a preferred embodiment, the solvent utilized in the method of the invention is an aromatic hydrocarbon solvent such as p-xylene (b.p. 137–138° C.) m-xylene (b.p.

139° C.) and o-xylene (b.p. 144° C.). In one embodiment, Reactions (I) or (II) is carried out in m-xylene at a temperature above 120° C. and preferably above 130° C. In another embodiment, Reaction (I) or (II) is carried out in o-xylene at a temperature above 120° C., and preferably above 135° C.

Preparation of the Group 15 Containing Metal Polymerization Catalyst Compound The Group 15 containing metal polymerization catalyst compounds may be prepared by reacting the neutral ligand, YLZ or YL'Z, prepared as described above, with a compound represented by the formula $M^nX_n$, as is known in the art. where M is a Group 3 to 14 metal, n is the oxidation state of M, each X is an anionic group, such as halide in a non-coordinating or weakly coordinating solvent, such as ether, toluene, xylene, benzene, methylene chloride, and/or hexane or other solvent having a boiling point at about 20° C. to about 150° C. and preferably 20° C. to 100° C., preferably for 24 hours or more, then treating the mixture with an excess (such as four or more equivalents) of a strong base, such as for example, lithiumdimethylamide ($LiN(CH_3)_2$), or an alkylating agent, such as for example methyl magnesium bromide in ether. The magnesium salts, if present, are removed by filtration. The resulting metal complex isolated by standard techniques. In a preferred embodiment the solvent has a boiling point above 60° C., such as toluene, xylene, benzene, and/or hexane. In another embodiment the solvent comprises ether and/or methylene chloride, either being preferable.

Activators and Activation Methods for Catalyst Compounds

The Group 15 containing metal polymerization catalyst compounds, prepared above, are typically combined with an activator compound to yield compounds having a vacant coordination site that will coordinate, insert, and polymerize olefin(s). For the purposes of this patent specification and appended claims, the term "activator" is defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts.

Aluminoxane and Aluminum Alkyl Activators

In one embodiment, alumoxanes activators are utilized as an activator in the catalyst composition of the invention. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. A another alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum alkyl or organoaluminum compounds which may be utilized as activators include trimethylaluminum, triethylaluminum, triisobutylaluminum, tri-n-hexylaluminum, tri-n-octylaluminum and the like.

Ionizing Activators

It is within the scope of this invention to use an ionizing or stoichiometric activator, neutral or ionic, such as tri (n-butyl) ammonium tetrakis (pentafluorophenyl) boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

In a preferred embodiment, the stoichiometric activators include a cation and an anion component, and may be represented by the following formula:

$$(L-H)_d^+ (A^{d-}) \tag{V}$$

wherein L is an neutral Lewis base;

H is hydrogen;

$(L-H)^+$ is a Bronsted acid $A^{d-}$ is a non-coordinating anion having the charge d− d is an integer from 1 to 3.

The cation component, $(L-H)_d^+$ may include Bronsted acids such as protons or protonated Lewis bases or reducible Lewis acids capable of protonating or abstracting a moiety, such as an akyl or aryl, from the bulky ligand metallocene or Group 15 containing transition metal catalyst precursor, resulting in a cationic transition metal species.

The activating cation $(L-H)_d^+$ may be a Bronsted acid, capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene and mixtures thereof. The activating cation $(L-H)_d^+$ may also be an abstracting moiety such as silver, carboniums, tropylium, carbeniums, ferroceniums and mixtures, preferably carboniums and ferroceniums. Most preferably $(L-H)_d^+$ is triphenyl carbonium.

The anion component $A^{d-}$ include those having the formula $[M^{k+} Q_n]^{d-}$ wherein k is an integer from 1 to 3; n is an integer from 2–6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Supports, Carriers and General Supporting Techniques

The Group 15 containing metal polymerization catalyst compound, prepared in accordance with the invention may be combined with a support material or carrier, or with a supported activator. For example, the catalyst compound is deposited on, contacted with, vaporized with, bonded to, or incorporated within, adsorbed or absorbed in, or on, a support or carrier.

The support material is any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference. A preferred support is fumed silica available under the trade name Cabosil™ TS-610, available from Cabot Corporation. Fumed silica is typically a silica with particles 7 to 30 nanometers in size that has been treated with dimethylsilyldichloride such that a majority of the surface hydroxyl groups are capped.

It is preferred that the support material, most preferably an inorganic oxide, has a surface area in the range of from about 10 to about 700 m²/g, pore volume in the range of from about 0.1 to about 4.0 cc/g and average particle size in the range of from about 5 to about 500 μm. More preferably, the surface area of the support material is in the range of from about 50 to about 500 m²/g, pore volume of from about 0.5 to about 3.5 cc/g and average particle size of from about 10 to about 200 μm. Most preferably the surface area of the support material is in the range is from about 100 to about 400 m²/g, pore volume from about 0.8 to about 3.0 cc/g and average particle size is from about 5 to about 100 μm. The average pore size of the carrier of the invention typically has pore size in the range of from 10 to 1000 Å, preferably 50 to about 500 Å, and most preferably 75 to about 350 Å.

EXAMPLES

In order to provide a better understanding of the present invention including representative advantages thereof, the following example is offered.

Example 1

Preparation of $[(2,4,6\text{-Me}_3C_6H_2)NHCH_2CH_2]_2NH$ at 135° C.

A 500 mL one-armed Schlenk flask was charged with a magnetic stir bar, diethylenetriamine (1.290 g, 12.50 mmol), 2-bromomesitylene (5.008 g, 25.15 mol), tris(dibenzylideneacetone)dipalladium (0.060 g, 0.066 mmol), racemic-2,2'-bis(diphenylphosphino)-1,1'-binaphthyl (racemic BINAP) (0.121 g, 0.194 mmol), sodium tert-butoxide (3.722 g, 38.72 mmol), and m-xylene (400 mL) under dry, oxygen-free nitrogen. The reaction mixture was stirred and heated to 135° C. After 6 h the reaction was complete, as judged by proton NMR spectroscopy. All remaining manipulations can be performed in air. All solvent was removed under vacuum with heat and the residues dissolved in diethyl ether (500 mL). The ether was washed with water (3×100 mL) followed by saturated aqueous NaCl (90 g in 250 mL) and dried over magnesium sulfate (15 g). Removal of the ether in vacuo yielded a red oil which was dried at 70° C. for 12 h under vacuum. $^1$H NMR ($C_6D_6$) δ 6.83 (s, 4), 3.39 (br s, 2), 2.86 (t, 4), 2.49 (t, 4), 2.27 (s, 12), 2.21 (s, 6), 0.68 (br s, 1).

Example 2

Preparation of $[(2,4,6\text{-Me}_3C_6H_2)NHCH_2CH_2]_2NH$ at 140° C.

A 500 mL one-armed Schlenk flask was charged with a magnetic stir bar, diethylenetriamine (1.290 g, 12.50 mmol), 2-bromomesitylene (5.012 g, 25.17 mol), tris(dibenzylideneacetone)dipalladium (0.062 g, 0.068 mmol), racemic-2,2'-bis(diphenylphosphino)-1,1'-binaphthyl (racemic BINAP) (0.123 g, 0.197 mmol), sodium tert-butoxide (3.732 g, 38.82 mmol), and o-xylene (400 mL) under dry, oxygen-free nitrogen. The reaction mixture was stirred and heated to 140° C. After 6 h the reaction was complete, as judged by proton NNM spectroscopy. All remaining manipulations can be performed in air. All solvent was removed under vacuum with heat and the residues dissolved in diethyl ether (500 mL). The ether was washed with water (3×100 mL) followed by saturated aqueous NaCl (90 g in 250 mL) and dried over magnesium sulfate (15 g). Removal of the ether in vacuo yielded a red oil which was dried at 70° C. for 12 h under vacuum. $^1$H NMR ($C_6D_6$) δ 6.83 (s, 4), 3.39 (br s, 2), 2.86 (t, 4), 2.49 (t, 4), 2.27 (s, 12), 2.21 (s, 6), 0.68 (br s, 1).

We claim:

1. A method of preparing a Group 15 containing metal polymerization catalyst compound comprising:

a) preparing a ligand in accordance with Reaction (I) conducted at a temperature above 120° C., in the presence of a transition metal catalyst and a base

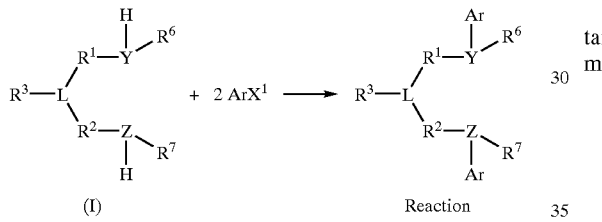

(I)    Reaction wherein:
   L is a Group 15 or 16 element;
   Y is Group 15 element;
   Z is a Group 15 element;
   $R^1$ and $R^2$ are independently a $C_1$ to $C_{20}$ hydrocarbon group, a heteroatom containing group having up to twenty carbon atoms, silicon, germanium, tin, lead, or phosphorus;
   each $R^3$ is independently hydrogen, a hydrocarbon group, a halogen, or a heteroatom containing group;
   Ar is an aromatic group; and
   each $X^1$ is a leaving group; and b) combining the ligand prepared in step a) with a compound represented by the formula $M^nX_n$ where M is a Group 3 to 14 metal, n is the oxidation state of M, each X is an anionic group.

2. The method of claim 1 wherein step a) is conducted at a temperature above 130° C.

3. The method of claim 1 wherein L, Y and Z are a Group 15 element.

4. The method of claim 1 wherein $R^1$ and $R^2$ are independently a linear, branched or cyclic $C_2$ to $C_{20}$ alkyl group.

5. The method of claim 1 wherein L, Y, and Z are nitrogen, $R^1$ and $R^2$ are a hydrocarbon radical, and $R^3$, $R^6$ and $R^7$ are hydrogen.

6. The method of claim 1 wherein Ar of aromatic compound $ArX^1$ is represented by the formula:

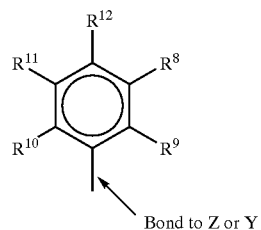

Bond to Z or Y wherein $R^8$ to $R^{12}$ are each independently hydrogen, a $C_1$ to $C_{40}$ alkyl group, a halide, a heteroatom, a heteroatom containing group containing up to 40 carbon atoms, preferably a $C_1$ to $C_{20}$ linear or branched alkyl group, preferably a methyl, ethyl, propyl or butyl group, any two R groups may form a cyclic group and/or a heterocyclic group. The cyclic groups may be aromatic.

7. The method of claim 6 wherein $R^9$, $R^{10}$ and $R^{12}$ are independently a methyl, ethyl, propyl or butyl group.

8. The method of claim 6 wherein $R^9$, $R^{10}$ and $R^{12}$ are methyl groups, and $R^8$ and $R^{11}$ are hydrogen.

9. The method of claim 1 wherein each X is independently selected from the group consisting of hydrogen, a alkyl group, a heteroatom, a halogen, and combinations thereof.

10. The method of claim 1 wherein M is a Group 4, 5 or 6 metal.

11. The method of claim 1 wherein the Group 15 containing metal catalyst compound is represented by the formulae:

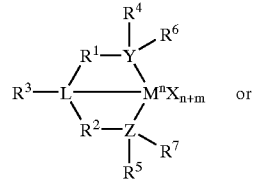

or wherein M a Group 4, 5 or 6 metal;
   each X is independently a leaving group;
   n is the oxidation state of M;
   m is the formal charge of the YLZ or the YL'Z ligand;
   L is a Group 15 or 16 element;
   Y is a Group 15 element;
   Z is a Group 15 element;
   $R^1$ and $R^2$ are independently a $C_1$ to $C_{20}$ hydrocarbon group, a heteroatom containing group having up to twenty carbon atoms, silicon, germanium, tin, lead, or phosphorus;
   $R^3$ is absent or a hydrocarbon group, hydrogen, a halogen, a heteroatom containing group;
   $R^4$ and $R^5$ are independently an alkyl group, an aryl group, substituted aryl group, a cyclic alkyl group, a substituted cyclic alkyl group, a cyclic arylalkyl group, a substituted cyclic arylalkyl group or multiple ring system;
   $R^1$ and $R^2$ may be interconnected to each other, and/or $R^4$ and $R^5$ may be interconnected to each other; and
   $R^6$ and $R^7$ are independently absent, or hydrogen, an alkyl group, halogen, heteroatom or a hydrocarbylgroup.

12. The method of claim 11 wherein L, Y, and Z are nitrogen, $R^1$ and $R^2$ are a hydrocarbon radical, $R^3$ is hydrogen, and $R^6$ and $R^7$ are absent.

13. The method of claim 6 wherein L and Z are independently nitrogen and $R^6$ and $R^7$ are absent.

14. The method of claim 1 wherein the transition metal catalyst is a palladium complex.

15. The method of claim 11 further comprising combining the Group 15 containing metal catalyst compound with an activator compound.

16. The method of claim 11 further comprising combining the Group 15 containing metal catalyst compound with a support material.

* * * * *